(12) United States Patent
Badylak (10) Patent No.: US 7,776,596 B2
(45) Date of Patent: *Aug. 17, 2010

(54) VASCULARIZATION ENHANCED GRAFT CONSTRUCTS

(75) Inventor: Stephen F. Badylak, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 362 days.

This patent is subject to a terminal disclaimer.

(21) Appl. No.: 10/428,358

(22) Filed: May 2, 2003

(65) Prior Publication Data

US 2004/0006395 A1 Jan. 8, 2004

Related U.S. Application Data

(60) Provisional application No. 60/377,573, filed on May 2, 2002.

(51) Int. Cl.
*A01N 63/00* (2006.01)
*A61K 35/22* (2006.01)
*A61K 35/37* (2006.01)
*C12N 5/00* (2006.01)
*C12N 5/08* (2006.01)

(52) U.S. Cl. .............. 435/373; 435/325; 435/371; 424/93.7; 424/551; 424/558

(58) Field of Classification Search ............ 424/93.7, 424/550, 558, 551; 435/325, 371, 373
See application file for complete search history.

(56) References Cited

U.S. PATENT DOCUMENTS

| | | | |
|---|---|---|---|
| 4,829,000 A | 5/1989 | Kleinman et al. | |
| 4,902,508 A | 2/1990 | Badylak et al. | |
| 4,956,178 A | 9/1990 | Badylak et al. | |
| 5,281,422 A | 1/1994 | Badylak et al. | |
| 5,352,463 A | 10/1994 | Badylak et al. | |
| 5,554,389 A | 9/1996 | Badylak et al. | |
| 5,641,518 A | 6/1997 | Badylak et al. | |
| 5,863,531 A | 1/1999 | Naughton et al. | |
| 5,885,619 A | 3/1999 | Patel et al. | |
| 5,945,101 A | 8/1999 | Berg et al. | |
| 5,955,110 A | 9/1999 | Patel et al. | |
| 6,022,743 A | 2/2000 | Naughton et al. | |
| 6,099,567 A | 8/2000 | Badylak et al. | |
| 6,171,344 B1 | 1/2001 | Atala | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,264,992 B1 | 7/2001 | Voytik-Harbin et al. | |
| 6,358,284 B1 | 3/2002 | Fearnot et al. | |
| 6,375,989 B1 | 4/2002 | Badylak et al. | |
| 6,379,710 B1 | 4/2002 | Badylak | |
| 6,419,920 B1 | 7/2002 | Mineau-Hanschke | |
| 6,475,232 B1 | 11/2002 | Babbs et al. | |
| 6,485,723 B1 * | 11/2002 | Badylak et al. | 424/93.7 |
| 6,918,396 B1 | 7/2005 | Badylak et al. | |
| 6,962,814 B2 | 11/2005 | Mitchell et al. | |
| 7,087,089 B2 | 8/2006 | Patel et al. | |
| 7,175,841 B2 * | 2/2007 | Badylak et al. | 424/93.7 |
| 2003/0113302 A1 | 6/2003 | Revazova et al. | |
| 2003/0216811 A1 | 11/2003 | Badylak | |
| 2003/0216812 A1 | 11/2003 | Badylak | |
| 2004/0006395 A1 | 1/2004 | Badylak | |
| 2005/0202058 A1 | 9/2005 | Hiles et al. | |
| 2006/0257377 A1 | 11/2006 | Atala et al. | |
| 2007/0141037 A1 | 6/2007 | Badylak et al. | |

FOREIGN PATENT DOCUMENTS

| | | |
|---|---|---|
| WO | 98/06445 A1 | 2/1998 |
| WO | WO 98/25637 | 6/1998 |
| WO | WO 98/52637 | 11/1998 |
| WO | WO 00/15765 A1 | 3/2000 |
| WO | WO 00/62833 A1 | 10/2000 |
| WO | WO 01/48153 A1 * | 1/2001 |
| WO | WO 01/10355 | 2/2001 |
| WO | WO 01/45765 | 6/2001 |

(Continued)

OTHER PUBLICATIONS

Nerem, R., 2006, Tissue Engineering, vol. 12, No. 5, p. 1143-1150.*

(Continued)

*Primary Examiner*—Shin-Lin Chen
(74) *Attorney, Agent, or Firm*—Barnes & Thornburg LLP (57) ABSTRACT

A tissue graft construct for use in repairing diseased or damaged tissues is provided. The tissue graft construct comprises a matrix composition selected from the group consisting of urinary bladder submucosa and stomach submucosa, and extracts and hydrolysates thereof, added endothelial cells, and at least one additional preselected, exogenous population of cells which enhance initiation of the formation vessel-like structures in the graft construct. The preselected population of cells can be a population of non-keratinized or keratinized epithelial cells or a population of mesodermally-derived cells selected from the group consisting of fibroblasts, smooth muscle cells, skeletal muscle cells, cardiac muscle cells, multi-potential progenitor cells, pericytes, osteogenic cells, and any other suitable cell type, preferably selected based on the tissue to be repaired. Methods for enhancing the vascularization in vivo of these tissue graft constructs and for preparing these graft constructs are also provided.

26 Claims, 3 Drawing Sheets

FOREIGN PATENT DOCUMENTS

| WO | WO 01/48153 A1 | 7/2001 |
| WO | WO 01/78754 | 10/2001 |
| WO | WO 02/07646 A2 | 1/2002 |
| WO | WO 02/14480 | 2/2002 |
| WO | WO 02/14480 A2 | 2/2002 |
| WO | WO 02/20729 A2 | 3/2002 |

OTHER PUBLICATIONS

"Endothelial Implants Inhibit Intimal Hyperplasia After Porcine Angioplasty," Helen M. Nugent et al., *Circulation Research*, Mar. 5, 1999, vol. 84, No. 4, p. 384-391.

"Three-Dimensional Imaging of Extracellular Matrix and Extracellular Matrix-Cell Interactions," Voytik-Harbin et al., Methods in Cell Biology, Ch. 27, vol. 43, pp. 583-597.

"Time-Lapse Confocal Reflection Microscopy of Collagen Fibrillogenesis and Extracellular Matrix Assembly In Vitro," A.O. Brightman et al., *Biopolymers*, vol. 54, 2000, pp. 222-234.

"Basal Lamina of Avian Ovarian Follicle: Influence On Morphology of Granulosa Cells In-Vitro," E.K. Asem et al., *Comparative Biochemistry and Physiology, Part C*, 125 (2000), pp. 189-201.

"Effect of Basal Lamina on Progesterone Production by Chicken Granulosa Cells in Vitro—Influence of Follicular Development," E.K. Asem et al., *Comparative Biochemistry and Physiology, Part C*, 125 (2000), pp. 233-244.

"PDGF, TGF-β, and Heterotypic Cell-Cell Interactions Mediate Endothelial Cell-Induced Recruitment of 10T1/2 Cells and Their Differentiation To A Smooth Muscle Fate," K.K. Hirschi et al., *The Journal of Cell Biology*, vol. 141, No. 3, May 4, 1998, pp. 805-814.

"Endothelial Cell Influences on Vascular Smooth Muscle Phenotype," J.H. Campbell et al., *Ann. Rev. Physiol.*, 1986, vol. 48, pp. 295-306.

Badylak et al., "Endothelial cell adherence to small intestinal submucosa: an acellular bioscaffold" *Biomaterials*, vol. 20, 1999, pp. 2257-2263.

Yang et al., "Tissue engineered artificial skin composed of dermis and epidermis", Artificial Organ, Jan. 2000, 24 (1):7-17.

Block, S., "Peroxygen Compounds," Sterilants, Disinfectants, and Antiseptics. A. By Chemical Type, S. Block, editor, 5th Edition 2001, pp. 185-204.

Denton, G.W., "Chlorhexidine," Sterilants, Disinfectants, and Antiseptics. A. By Chemical Type, S. Block, editor, 5th Edition 2001, pp. 321-336.

"Artificial Blood Vessel," English translation of Japanese Patent Application Publication No. 3-12169, 1991, 16 pages.

Bhatia et al., "Controlling Cell Interactions by Micropatterning in Co-Cultures: Hepatocytes and 3T3 Fibroblasts," Journal of Biomedical Materials Research, vol. 34, 1997, pp. 189-199.

Castano et al., "Inhibition of DNA Synthesis by Aspirin in Swiss 3T3 Fibroblasts," Journal of Pharmacology and Experimental Therapeutics, vol. 280, No. 1, 1997, pp. 366-372.

Ho et al., "Identification of Engothelial Cell Genes by Combined Database Mining and Microarray Analysis", Physiol Genomics, vol. 13, 2003, pp. 249-262.

"In Vivo Plant Material", English translation of Japanese Patent Application Publication No. 1-170466, 1989, 13 pages.

Keyes et al., "An In Vitro Tumor Model: Analysis of Angiogenic Factor Expression after Chemotherapy," Cancer Research, vol. 62, 2002, pp. 5597-5602.

Kubota Y. et al., "Role of Laminin and Basement Membrane in the Morphological Differentiation of Human Endothelial Cells into Capillary-like Structures," Journal of Cell Biology, vol. 107, 1988, pp. 1589-1598.

Liu et al., "Effects of Salvianolic Acid-A on NIH/3T3 Fibroblast Proliferation, Collagen Synthesis and Gene Expression," World J. Gastroentero, vol. 6, No. 3, 2000, pp. 361-364.

Maru et al., "An Oncogenic Form of the Flt-1 Kinase has a Tubulogenic Potential in a Sinusoidal Endothelial Cell Line," European Journal of Cell Biology, vol. 79, 2000, pp. 130-143.

Montesano "Paracrine Induction of Angiogenesis in Vitro by Swiss 3T3 Fibroblasts", Journal of Cell Science, vol. 105, 1993, pp. 1013-1024.

Nerem "Tissue Engineering: The Hope, The Hype and The Future" Tissue Engineering, vol. 12, No. 5, 2006, p. 1143-1150.

Russmann H. et al., "Translocation of *Yersinia enterocolitica* through an Endothelial Monolayer by Polymorphonuclear Leukocytes," Infection and Immunity, vol. 64, No. 3, 1996, pp. 1016-1019.

Office Action regarding Japanese Application Serial No. 2004-500578, Mailed from the Japanese Patent Office Aug. 25, 2009, pp. 1-4, English translation.

"Three Dimensional Imaging of Extracellular Matrix and Extracellular Matrix-Cell Interactions," Voytik-Harbin et al., Methods in Cell Biology, Ch. 27, vol. 43, pp. 583-597, 2001.

* cited by examiner

VASCULARIZATION ENHANCED GRAFT CONSTRUCTS

CROSS-REFERENCE TO RELATED APPLICATION

This application claims priority under 35 U.S.C. §119(e) to U.S. Provisional Application No. 60/377,573 filed May 2, 2002.

GOVERNMENT RIGHTS

Research relating to this invention was supported in part by the U.S. Government under Grant No. GM60691 awarded from the National Institutes of Health. The U.S. Government may have certain rights in this invention.

FIELD OF THE INVENTION

The present invention relates to vascularization enhanced tissue grafts derived from a matrix composition and their use in repairing diseased or damaged tissues. More particularly, this invention is directed to vascularization enhanced tissue grafts comprising a stomach submucosa or urinary bladder derived matrix composition that has been seeded with endothelial cells and at least one additional preselected, exogenous population of cells to enhance the repair capabilities of the tissue graft constructs.

BACKGROUND AND SUMMARY OF THE INVENTION

The present invention is directed to a tissue graft construct comprising a matrix composition seeded with endothelial cells and at least one additional preselected, exogenous cell population for use in the repair of damaged or diseased tissues. The matrix composition for use in accordance with the present invention is selected from the group consisting of urinary bladder submucosa and stomach submucosa, and extracts and hydrolysates thereof. The matrix composition preferably comprises highly conserved collagens, glycoproteins, proteoglycans, and glycosaminoglycans. The matrix composition for use in this invention is derived from urinary bladder or stomach tissue of a warm-blooded vertebrate.

The submucosa components of the present tissue graft constructs are substantially acellular matrices that provide a superior cell growth substrate resembling the matrix environment found in vivo. The natural composition and configuration of the matrix composition provides a unique cell growth substrate that promotes the attachment and proliferation of cells in vitro and induces tissue remodeling when the graft constructs are implanted in vivo.

As tissue graft materials, urinary bladder submucosa and stomach submucosa induce the growth of endogenous tissues upon implantation into a host (i.e., the graft materials induce remodeling). When used in such an application the tissue graft constructs appear not only to serve as a matrix for the growth or regrowth of the tissues replaced by the graft constructs, but also to promote or to induce such growth or regrowth of endogenous tissue. These graft materials can be used in an implantable sheet form or in injectable fluidized or gel forms for inducing the regrowth of endogenous tissues.

The present invention is directed to tissue graft constructs comprising a matrix composition selected from the group consisting of urinary bladder submucosa and stomach submucosa, and extracts and hydrolysates thereof, and further including added endothelial cells and at least one additional preselected, exogenous population of cells. The invention is also directed to methods of enhancing the vascularization of a tissue graft construct in vivo. The vascularization enhanced tissue graft constructs are prepared by seeding the matrix composition in vitro with endothelial cells or endothelial cell precursors (e.g., progenitor cells or stem cells) and at least one additional preselected or predetermined cell type prior to implanting or injecting the tissue graft construct into the host.

One embodiment provides a tissue graft construct for use in repairing diseased or damaged tissues. The tissue graft construct comprises a matrix composition selected from the group consisting of urinary bladder submucosa and stomach submucosa, and extracts and hydrolysates thereof, added endothelial cells, and at least one additional preselected, exogenous population of cells.

In another embodiment a vascularized tissue graft construct is provided for use in repairing diseased or damaged tissues. The tissue graft construct comprises a matrix composition selected from the group consisting of urinary bladder submucosa and stomach submucosa, and extracts and hydrolysates thereof, added endothelial cells, and at least one additional preselected, exogenous population of cells wherein the endothelial cells have been cultured on the matrix composition for a time sufficient to form vessels or vessel-like structures in vitro.

In another embodiment a method is provided for enhancing the vascularization in vivo of a tissue graft construct. The method comprises the steps of seeding in vitro a matrix composition selected from the group consisting of urinary bladder submucosa and stomach submucosa, and extracts and hydrolysates thereof, with a population of endothelial cells and at least one additional preselected, exogenous population of cells to form the graft construct, and implanting the graft construct into a vertebrate at a site in need of repair.

In yet another embodiment a method is provided for enhancing the vascularization in vivo of a tissue graft construct. The method comprises the steps of seeding in vitro a matrix composition selected from the group consisting of urinary bladder submucosa and stomach submucosa, and extracts and hydrolysates thereof, with a population of endothelial cells and at least one additional preselected, exogenous population of cells, culturing in vitro the endothelial cells for a time sufficient to induce the formation of vessels or vessel-like structures or components, and implanting the graft construct into a vertebrate in a site in need of repair.

In either of these method embodiments the matrix composition can be seeded with the additional preselected population of cells after the matrix composition is seeded with the endothelial cells, the matrix composition can be seeded with the additional preselected population of cells before the matrix composition is seeded with the endothelial cells, or the matrix composition can be seeded with the endothelial cells and the additional preselected population of cells simultaneously or nearly simultaneously.

The endothelial cells can be cultured in vitro on the matrix composition for a time sufficient to induce the formation of vessels or vessel-like structures, or the endothelial cells can be cultured on the matrix composition for a time sufficient to expand the endothelial cells (i.e., allow the endothelial cells to divide at least one time) without forming vessels or vessel-like structures in vitro. Alternatively, the graft construct can be implanted without expanding the endothelial cells. In any of these embodiments the additional preselected population of cells may or may not be expanded (i.e., allowed to progress through at least one cell division cycle) prior to implanting the graft construct.

In still another embodiment a method is provided of preparing a tissue graft construct for use in repairing diseased or damaged tissues. The method comprises the step of seeding in vitro a matrix composition selected from the group consisting of urinary bladder submucosa and stomach submucosa, and extracts and hydrolysates thereof, with a population of endothelial cells, and at least one additional preselected, exogenous population of cells to form the graft construct. The method can further comprise the step of culturing the endothelial cells in vitro on the matrix composition for a time sufficient to induce the formation of vessels or vessel-like structures.

In any of these embodiments the at least one additional cell population can comprise a population of non-keratinized or keratinized epithelial cells or a population of mesodermally derived cells selected from the group consisting of fibroblasts, smooth muscle cells, skeletal muscle cells, cardiac muscle cells, multi-potential progenitor cells (e.g., stem cells), pericytes, and osteogenic cells. In various embodiments, the matrix composition can be seeded with endothelial cells and one or more of these additional cell types (i.e., the matrix composition can be seeded with endothelial cells and one, two, three, etc. of these additional cell types).

DETAILED DESCRIPTION OF THE INVENTION

The present invention is directed to a tissue graft construct comprising a matrix composition selected from the group consisting of urinary bladder submucosa and stomach submucosa, and extracts and hydrolysates thereof, and further including added endothelial cells and at least one additional preselected, exogenous population of cells. The matrix composition is seeded with the endothelial cells and the preselected, exogenous population(s) of cells, and is used to repair diseased or damaged tissues. In accordance with the invention "damaged tissues" means tissues which are injured, lacerated, severed, or that have been surgically removed or are otherwise missing from the site in need of repair (e.g., congenital absence or deformity). The matrix composition is preferably prepared from an extracellular matrix composition derived from a tissue selected from the group consisting of urinary bladder submucosa and stomach submucosa, and extracts and hydrolysates thereof. The endothelial cells for use in accordance with the invention can be derived from any type of endothelial cell population including macrovascular, microvascular, arterial, and venous endothelial cells. Either mature endothelial cells (e.g., harvested from an organ or a blood vessel) or endothelial cell precursors (e.g., progenitor cells or stem cells) can be used in accordance with the invention. Additionally, the endothelial cells can be harvested from a young or an old animal, but endothelial cells harvested from a young animal are preferred.

In one embodiment the additional preselected, exogenous population(s) of cells can comprise a population of non-keratinized or keratinized epithelial cells or a population of mesodermally-derived cells selected from the group consisting of fibroblasts, smooth muscle cells, skeletal muscle cells, cardiac muscle cells, multi-potential progenitor cells, pericytes, osteogenic cells, or any other suitable cell type.

The additional preselected, exogenous population of cells, which is combined with the matrix composition and the endothelial cells, can be selected based on the cell type of the intended tissue to be repaired. For example, if skin is to be repaired, the preselected, exogenous population of cells can be non-keratinized epithelial cells or if cardiac tissue is to be repaired, the preselected, exogenous population of cells can be cardiac muscle cells. In another embodiment the matrix composition is seeded with autogenous cells isolated from the patient to be treated.

In one embodiment, the at least one additional preselected population of cells to be combined with the matrix composition and the endothelial cells includes smooth muscle cells and/or progenitor cells capable of differentiating into smooth muscle cells. Advantageously, the smooth muscle cells and/or smooth muscle progenitor cells can promote, along with the endothelial cells, the formation of vessels or vessel-like structures in the graft construct. In another embodiment, additional cell types can be added along with endothelial cells, smooth muscle cells, and/or smooth muscle cell progenitor cells.

In still another embodiment the at least one additional preselected, exogenous population of cells comprises a population of multi-potential progenitor cells. The matrix composition can induce the differentiation of these multi-potential progenitor cells into cells that assist in the repair of damaged tissues. Advantageously, the matrix composition seeded with a population of endothelial cells and a population of multi-potential progenitor cells can be implanted into a variety of different in vivo locations and the progenitor cells will differentiate into the appropriate cell type for the specific environment. For example, implantation of a composition comprising endothelial cells and multi-potential progenitor cells at the site of a tendon or a ligament will result in the graft construct remodeling into a tendon or a ligament.

The combination of the matrix composition, endothelial cells, and an additional preselected, exogenous population of cells provides a tissue graft construct that shows surprisingly enhanced vascularization in vitro and/or in vivo leading to improved wound healing capabilities and better restoration of tissue function compared to the use of either the matrix composition alone, in combination with endothelial cells alone, or in combination with cell types other than endothelial cells as therapeutic agents.

Figure 1:
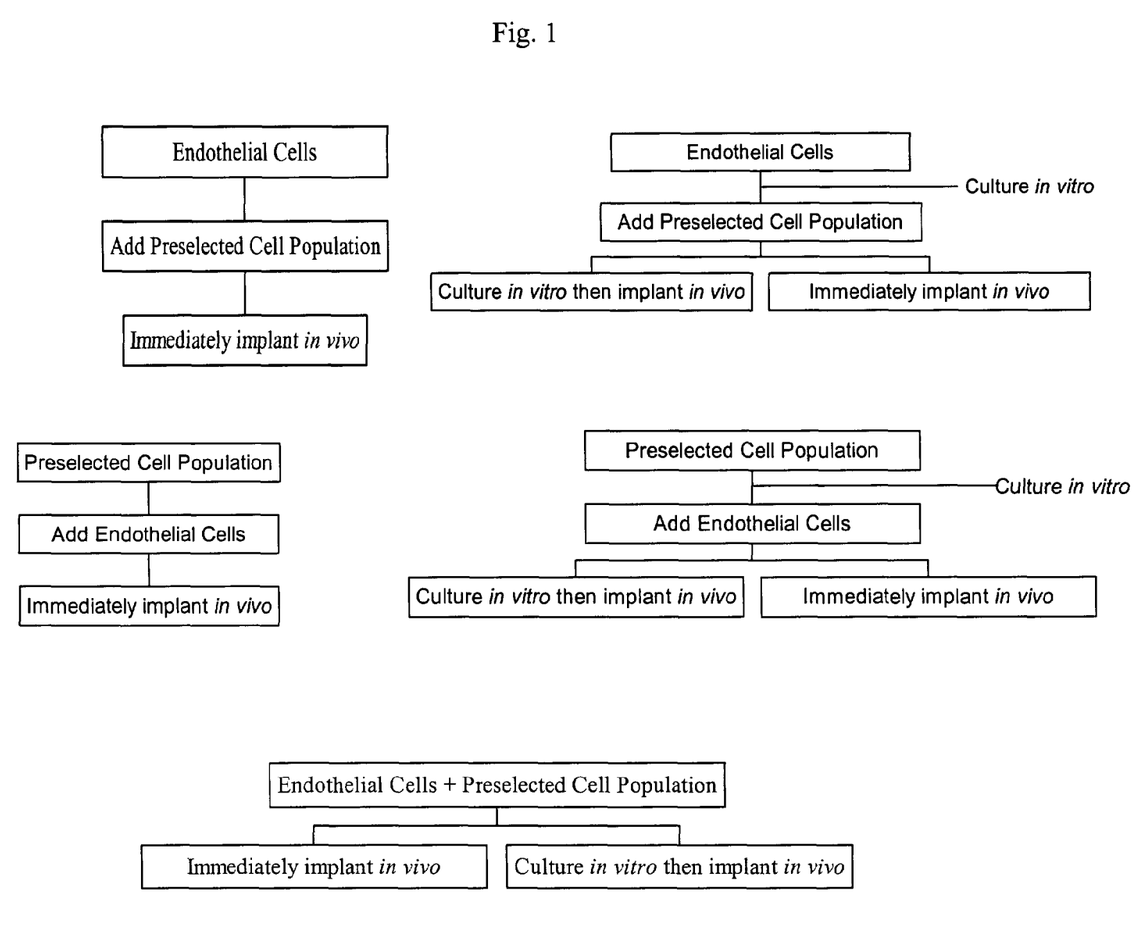
FIG. 1 provides flow charts depicting alternative preparations of the present graft constructs.

In various embodiments, the matrix composition can be seeded with the additional preselected population of cells after the matrix composition is seeded with the endothelial cells, the matrix composition can be seeded with the additional preselected population of cells before the matrix composition is seeded with the endothelial cells, or the matrix composition can be seeded with the endothelial cells and the additional preselected population of cells simultaneously or nearly simultaneously (see FIG. 1 for various exemplary embodiments).

In one such embodiment, the matrix composition can be seeded with endothelial cells and the endothelial cells can be cultured on the matrix composition prior to the implantation of the construct into the affected region for a time sufficient to induce the formation of vessels or vessel-like structures. The matrix composition can be seeded with the at least one additional preselected, exogenous population of cells after the matrix composition is seeded with the endothelial cells and at any time up to just prior to implantation of the graft construct in vivo. Accordingly, depending on the time allowed for culturing the preselected population of cells on the matrix composition prior to implantation of the graft construct, the additional preselected population of cells may or may not be expanded (i.e., allowed to progress through at least one cell division cycle) prior to implantation of the graft construct into the affected region.

Alternatively, the matrix composition can be seeded with the at least one additional preselected, exogenous population of cells after the matrix composition is seeded with the endothelial cells, and the endothelial cells can be cultured on the matrix composition to expand the endothelial cells without inducing the formation of vessels or vessel-like structures or components prior to implantation of the graft. In this embodiment, depending on the time allowed for culturing the preselected population of cells on the matrix composition prior to implantation of the graft construct, the additional preselected population of cells may or may not be expanded prior to implantation of the graft construct into the affected region.

In another embodiment, the matrix composition can be seeded with the at least one additional preselected, exogenous population of cells after the matrix composition is seeded with the endothelial cells and the matrix composition can be implanted soon thereafter without expansion of either the endothelial cells or the additional preselected, exogenous population of cells.

In an alternate embodiment, the matrix composition can be seeded with the additional preselected, exogenous population of cells and the preselected population of cells can be cultured on the matrix composition to expand (i.e., allow the cells to divide at least one time) the preselected cell population prior to implantation of the graft construct. In this embodiment, the matrix composition can be seeded with the endothelial cells after the matrix composition is seeded with the preselected population of cells and at any time up to just prior to implantation of the graft in vivo. Accordingly, depending on the time allowed for culturing the endothelial cells on the matrix composition prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the matrix composition can be seeded with the endothelial cells after the matrix composition is seeded with the at least one additional preselected, exogenous population of cells and the graft can be implanted soon thereafter without expansion of either the endothelial cells or the additional preselected, exogenous population of cells.

In yet another embodiment, the matrix composition can be seeded simultaneously or nearly simultaneously with the endothelial cells and the additional preselected, exogenous population of cells. In this embodiment, the endothelial cells and the additional preselected, exogenous population of cells can be cultured on the matrix composition to expand the two cell populations or the graft can be implanted without expansion of the two cell populations. If the endothelial cells are expanded, the expansion of the endothelial cells may or may not include the formation of vessels or vessel-like structures.

A matrix composition selected from the group consisting of urinary bladder submucosa and stomach submucosa, and extracts and hydrolysates thereof, advantageously provides a physiological environment that supports the proliferation and differentiation of cells cultured in vitro on the matrix composition. Thus, cells can be seeded onto the matrix composition and can be cultured using standard cell culture techniques, as described below, known to those of ordinary skill in the art, to produce tissue grafts for implantation into a host in need thereof.

The ability of a matrix composition selected from the group consisting of urinary bladder submucosa and stomach submucosa, and extracts and hydrolysates thereof, to provide a substrate that supports the growth of cells provides the opportunity to expand the population of endothelial cells and/or the additional preselected, exogenous population of cells prior to implantation into a host. If endothelial cells are expanded, such expansion can result in the formation of vessels or vessel-like structures (i.e., potential vascularization of the graft construct in vitro) prior to implantation improving the wound healing capabilities of the graft upon implantation of the graft construct. The formation of vessels or vessel-like structures prior to implantation of the graft construct or, alternatively, the expansion of endothelial cells prior to implantation of the graft construct improves the wound healing capabilities of the graft upon implantation such as by promoting differentiation and migration of cells growing on the abluminal side of a urinary bladder or stomach submucosa tissue sheet and by promoting proliferation of these cells within the submucosa tissue itself.

In embodiments where the added endothelial cells, and the additional preselected, exogenous population of cells are cultured on the matrix composition prior to implantation, the cells are cultured on the matrix composition under conditions conducive to cell growth. The cultured cells can be in either direct or indirect contact (e.g., fluid communication) with the matrix composition. Conditions conducive to cell growth are environmental conditions, such as sterile technique, temperature (e.g., about 37° C.) and nutrient supply, that are considered optimal for cell growth under currently accepted procedures for tissue and cell culture. Although optimum culture conditions depend on the particular cell type, cell growth conditions are generally well known in the art.

Matrix compositions in accordance with the invention can be used in a variety of forms as a graft material and to culture endothelial cells and other cell types in vitro prior to implantation of the graft construct. These forms include a sheet-like configuration, a gel form, a fluidized composition (e.g., by comminuting or digesting the tissue), and an extract for addition to art-recognized cell/tissue culture media. The matrix composition or component(s) thereof can provide a surface for cell adhesion and/or can induce cell differentiation and/or proliferation. The matrix composition is preferably sterilized prior to use in tissue/cell culture applications, however, non-sterile compositions can be used if antibiotics are included in the cell culture media.

In accordance with one embodiment of the present invention a urinary bladder or stomach submucosa tissue graft construct wherein the submucosa tissue is delaminated from the tunica muscularis layer and at least the luminal portion of the tunica mucosa layer of the submucosa tissue is used as a graft material and to culture endothelial cells and other cell types in vitro prior to implantation of the graft construct. Urinary bladder or stomach submucosa tissue delaminated in this manner can be used in accordance with the invention in sheet form, in a gel form, or as a fluidized composition such as a digest, or as an extract.

In one embodiment cells are seeded directly onto sheets of urinary bladder or stomach submucosa tissue under conditions conducive to cell proliferation for culture of the cells prior to implantation of the graft construct. The porous nature of these tissues allows diffusion of cell nutrients throughout the matrix. Thus, cells can be seeded onto and cultured on the luminal and/or the abluminal surface of the urinary bladder or stomach submucosa tissue sheets. The luminal surface of the urinary bladder or stomach submucosa tissue is the surface facing the lumen of the organ and is typically adjacent to an inner mucosa layer in vivo whereas the abluminal surface is the surface facing away from the lumen of the organ and is typically in contact with smooth muscle tissue in the organ source.

Cells cultured on solid sheets of submucosa tissue display a different growth pattern, and exhibit different interactions with the submucosa growth substrate, depending on which side of the submucosa sheet the cells are grown. Histological examination of endothelial cells cultured on submucosa tissue sheets reveals that the endothelial cells that are seeded onto the abluminal surface not only grow/proliferate along the surface of the submucosa tissue, but they also more readily migrate into and proliferate within the submucosa tissue itself. The luminal surface of the submucosa tissue comprises a more dense matrix than the abluminal side and, thus, cells are less likely to penetrate the luminal surface. Cells that are seeded onto the luminal surface of the submucosa tissue attach to the matrix but usually do not penetrate the surface of the matrix.

The endothelial cells and/or the additional preselected, exogenous population of cells seeded onto the matrix composition for culture prior to implantation of the graft construct can be grown in the presence of nutrients, including minerals, amino acids, sugars, peptides, proteins, or glycoproteins, such as laminin and fibronectin, and/or growth factors such as epidermal growth factor, vascular endothelial cell-derived growth factor, platelet-derived growth factor, platelet-derived growth factor-like molecules, transforming growth factor β, fibroblast growth factor, or another serum growth factor. In one embodiment fluidized or powder forms of the matrix composition can be used to supplement standard cell culture media to enhance the capacity for sustaining and inducing the proliferation of the cells in vitro and to induce remodeling in vivo. The cells can be grown on the matrix composition in the presence of commercially available cell culture liquid media (either serum-containing or serum-free).

In one embodiment, the at least one additional preselected population of cells to be combined with the matrix composition and the endothelial cells can be smooth muscle cells and/or progenitor cells capable of differentiating into smooth muscle cells to promote, along with the endothelial cells, the formation of vessels or vessel-like structures in the graft construct. It is known that treatment of smooth muscle cells with a heparinase can induce a phenotypic change characteristic of proliferating cells. Accordingly, in embodiments where the matrix composition is seeded with endothelial cells and at least one preselected, exogenous population of cells including a smooth muscle cell population and/or a smooth muscle cell progenitor cell population a heparinase can be included in the cell culture medium. For example, 4 units/ml of a heparinase from *Flavobaterium heparinum* can be included in the culture medium for a short interval (e.g., 6 hours) or can be present continually in the culture medium.

It is also known that smooth muscle cells that are seeded on a substrate as a subconfluent monolayer of cells undergo a phenotypic change associated with the capacity to divide. The phenotypic change is inhibited if the smooth muscle cells are co-cultured with a confluent monolayer of endothelial cells. Accordingly, in embodiments where the matrix composition is seeded with endothelial cells and at least one preselected, exogenous population of cells including a smooth muscle cell population and/or a smooth muscle cell progenitor cell population the added endothelial cells can be seeded onto the matrix composition so that the cells attach to the matrix composition as a subconfluent monolayer of cells. In another embodiment the endothelial cells, smooth muscle cells, and/or smooth muscle progenitor cells can be seeded onto the matrix composition so that the cells attach to the matrix composition as subconfluent monolayers of cells.

It has been well documented that submucosa tissue is capable of inducing host tissue proliferation, remodeling and regeneration of appropriate tissue structures upon implantation in a number of microenvironments in vivo (e.g., tendon, ligament, bone, articular cartilage, artery, and vein). The use of urinary bladder and stomach submucosa tissue in sheet form and fluidized forms for inducing the formation of endogenous tissues is described and claimed in U.S. Pat. Nos. 5,554,389, 6,099,567, and 6,264,992, the disclosures of which are expressly incorporated by reference. Thus, the urinary bladder or stomach submucosa tissue grafts in accordance with the invention are implanted in vivo to induce remodeling of damaged tissues in need of repair.

In one embodiment, the claimed compositions comprising the matrix composition, added endothelial cells, and an additional preselected, exogenous population of cells can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (*Science*, Vol. 210, pp. 908-910). Indeed, urinary bladder or stomach submucosa itself could be used advantageously to encapsulate the cells on a matrix in accordance with this invention for implantation as an artificial organ.

In one embodiment, a method is provided for enhancing the vascularization in vivo of a tissue graft construct. The method comprises the steps of seeding in vitro a matrix composition selected from the group consisting of urinary bladder submucosa and stomach submucosa, and extracts and hydrolysates thereof, with a population of endothelial cells and at least one additional preselected, exogenous population of cells to form the graft construct, and implanting the graft construct into a vertebrate at a site in need of repair. In one embodiment of this method, the matrix composition can be seeded with endothelial cells and the endothelial cells can be cultured on the matrix composition prior to the implantation of the construct into the affected region for a time sufficient to induce the formation of vessels or vessel-like structures. The matrix composition can be seeded with the at least one additional preselected, exogenous population of cells after the graft is seeded with the endothelial cells and at any time up to just prior to implantation of the graft in vivo. Accordingly, depending on the time allowed for culturing the preselected population of cells on the matrix composition prior to implantation of the graft construct, the additional preselected population of cells may or may not be expanded prior to implantation of the graft construct into the affected region.

Alternatively, the matrix composition can be seeded with the at least one additional preselected, exogenous population of cells after the matrix composition is seeded with the endothelial cells, and the endothelial cells can be cultured on the matrix composition to expand the endothelial cells without inducing the formation of vessels or vessel-like structures prior to implantation of the graft. In this embodiment, depending on the time allowed for culturing the endothelial cells on the matrix composition prior to implantation of the graft construct, the additional preselected population of cells may or may not be expanded prior to implantation of the graft construct into the affected region.

In another embodiment, the matrix composition can be seeded with the at least one additional preselected, exogenous population of cells after the matrix composition is seeded with the endothelial cells and the graft can be implanted soon thereafter without expansion of either the endothelial cells or the additional preselected, exogenous population of cells.

In an alternate embodiment of this method, the matrix composition can be seeded with the additional preselected, exogenous population of cells and the preselected population of cells can be cultured on the matrix composition to expand the preselected cell population prior to implantation of the graft construct. In this embodiment, the matrix composition can be seeded with the endothelial cells after the matrix composition is seeded with the preselected population of cells and at any time up to just prior to implantation of the graft in vivo. Accordingly, depending on the time allowed for expansion of the endothelial cells by culturing the cells on the matrix composition prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the matrix composition can be seeded with the endothelial cells after the matrix composition is seeded with the at least one additional preselected, exogenous population of cells and the graft can be implanted soon thereafter without expansion of either the endothelial cells or the additional preselected, exogenous population of cells.

In yet another embodiment, the matrix composition can be seeded simultaneously or nearly simultaneously with the endothelial cells and the additional preselected, exogenous population of cells. In this embodiment, the endothelial cells and the additional preselected, exogenous population of cells can be cultured on the matrix composition to expand the two cell populations or the graft can be implanted without expansion of the two cell populations. If the endothelial cells are expanded, the expansion of the endothelial cells may or may not include the formation of vessels or vessel-like structures.

A vascularized tissue graft construct for use in repairing diseased or damaged tissues is also provided in accordance with the invention. The vascularized graft construct comprises a matrix composition selected from the group consisting of urinary bladder submucosa and stomach submucosa, and extracts and hydrolysates thereof, and further includes added endothelial cells, and at least one additional preselected, exogenous population of cells wherein the endothelial cells have been cultured on the matrix composition for a time sufficient to form vessels or vessel-like structures in vitro.

In another embodiment, a method is provided for enhancing the vascularization in vivo of a tissue graft construct. The method comprises the steps of seeding a matrix composition selected from the group consisting of urinary bladder submucosa and stomach submucosa, and extracts and hydrolysates thereof, in vitro with a population of endothelial cells and at least one additional preselected, exogenous population of cells, culturing in vitro the endothelial cells and the additional cell population on the matrix composition for a time sufficient to induce the formation of vessels or vessel-like structures, and implanting the graft construct into a vertebrate in a site in need of repair.

Matrix compositions in accordance with the invention can be seeded with initially small cell populations that can be expanded in vitro prior to implantation. Advantageously, seeding with endothelial cells can induce vascularization of the grafts in vitro upon culturing the endothelial cells in vitro on the matrix composition. The matrix composition can be further seeded with smooth muscle cells or smooth muscle cell progenitor cells or another cell type, such as fibroblasts, to promote vascularization.

In this embodiment, the matrix composition is seeded with endothelial cells and the endothelial cells are cultured on the matrix composition prior to the implantation of the construct into the affected region for a time sufficient to induce the formation of vessels or vessel-like structures. The matrix composition can be seeded with the at least one additional preselected, exogenous population of cells after the matrix composition is seeded with the endothelial cells and at any time up to just prior to implantation of the graft in vivo. Accordingly, depending on the time allowed for culturing the preselected population of cells on the matrix composition prior to implantation of the graft, the additional preselected population of cells may or may not be expanded prior to implantation of the graft construct into the affected region.

In an alternate embodiment, the matrix composition can be seeded with the additional preselected, exogenous population of cells and the preselected population of cells can be cultured on the matrix composition to expand the preselected cell population prior to implantation of the graft construct. In this embodiment, the matrix composition is seeded with endothelial cells after the matrix composition is seeded with the preselected population of cells. In this embodiment, the endothelial cells are cultured on the matrix composition for a time sufficient to allow for expansion of the endothelial cells to form vessel or vessel-like structures prior to implantation of the graft construct into the affected region.

In another embodiment, the matrix composition can be seeded with the endothelial cells and the additional preselected, exogenous population of cells simultaneously or nearly simultaneously. In this embodiment, the additional preselected, exogenous population of cells and the endothelial cells are cultured on the matrix composition to expand the two cell populations prior to implantation of the graft.

A method of preparing a tissue graft construct for use in repairing diseased or damaged tissues is also provided. The method comprises the step of seeding in vitro a matrix composition selected from the group consisting of urinary bladder submucosa and stomach submucosa, and extracts and hydrolysates thereof, with a population of endothelial cells, and at least one additional preselected, exogenous population of cells to form the graft construct. The method can further comprise the step of culturing the endothelial cells on the matrix composition for a time sufficient to induce the formation of vessels or vessel-like structures prior to the implantation of the graft construct into the affected region.

The preparation of urinary bladder and stomach submucosa for use in accordance with this invention is described, for example, in U.S. Pat. Nos. 5,554,389 (urinary bladder submucosa) and 6,099,567 (stomach submucosa). To summarize, the submucosal tissues are prepared from vertebrate urinary bladder or stomach, preferably harvested from porcine, ovine or bovine species, but not excluding other species. In this regard, the submucosa tissues are typically xenogeneic (i.e., from a different species) but also may be allogeneic (i.e., from a nonidentical member of the same species) or autogeneic (i.e., from the same animal or individual).

In one method to prepare the urinary bladder and stomach submucosa tissues for use in the invention, the tissues are subjected to abrasion using a longitudinal wiping motion to remove the outer layers, comprising smooth muscle tissues, and the innermost layer, i.e., at least the luminal portion of the tunica mucosa. Thus, the submucosal tissue is delaminated from the tunica muscularis and at least the luminal portion of the tunica mucosa. In another embodiment, urinary bladder or stomach tissue can be prepared according to the method of Spievack described in WO 01/45765 incorporated herein by reference. According to this method urinary bladder or stomach tissue is soaked in a de-epithelializing solution such as 1 N saline, removing the epithelial cell layer and leaving all subadjacent layers including the epithelial basement membrane. Alternatively, urinary bladder or stomach tissue can be soaked in 1 N saline and subjected to enzymatic and mechanical delamination steps to remove additional layers, or portions thereof, subadjacent to the submucosal layer. Either of these procedures results in a preparation that includes the urinary bladder or stomach submucosa layer and the epithelial basement membrane.

The submucosa is then rinsed with saline and optionally sterilized; it can be stored in a hydrated or dehydrated state. Lyophilized or air dried submucosa can be rehydrated and used in accordance with this invention without loss of biological activity. Native submucosa as a starting material is a relatively acellular collagenous matrix and the preferred collagenous matrix composition prepared as described above is a collagenous matrix devoid of intact cells (i.e., the submucosa collagenous matrix composition is acellular).

To form multilayer sheets of submucosa, multiple layers of submucosa can be overlapped with each other. The individual layers can be fixed to one another using standard techniques known to those skilled in the art, including the use of sutures and biocompatible adhesives such as collagen binder pastes. Alternatively, layers may be fused together by compressing the overlapped regions under dehydrating conditions, optionally with the addition of heat as described in U.S. Pat. No. 5,711,969, the disclosure of which is expressly incorporated herein.

The vertebrate urinary bladder or stomach submucosa can be sterilized using conventional sterilization techniques including glutaraldehyde tanning, formaldehyde tanning at acidic pH, ethylene oxide treatment, propylene oxide treatment, gas plasma sterilization, gamma radiation, electron beam and peracetic acid sterilization. Preferred sterilization techniques include exposing the submucosa tissue to peracetic acid, 1-4 Mrads gamma irradiation (more preferably 1-2.5 Mrads of gamma irradiation) or gas plasma sterilization; peracetic acid sterilization is the most preferred sterilization method. Typically, the submucosa tissue is subjected to two or more sterilization processes. After the submucosa tissue is sterilized, for example by chemical treatment, the tissue can be sterilized again using electron beam or gamma irradiation sterilization techniques. Typically, the cells are added to the graft tissue after sterilization of the graft. A sterilization technique such as that described in U.S. Pat. No. 6,206,931, incorporated herein by reference, may also be used. The sterilized urinary bladder or stomach submucosa can be used to culture endothelial cells and the preselected cell population in vitro prior to implantation of the graft construct in accordance with the invention.

It is also known that vertebrate urinary bladder or stomach submucosa can be fluidized by comminuting and/or enzymatic digestion, without loss of its biological activity. See U.S. Pat. No. 6,264,992 B1 the disclosure of which is expressly incorporated herein by reference. More particularly, the native or fluidized submucosa composition can be treated with an enzyme for a period of time sufficient to solubilize all or a major portion of the submucosa components. Preferably the submucosa is digested with an enzyme that hydrolyzes the structural components of the submucosa to produce a suspension or homogenous solution of submucosa components. Submucosa can be enzymatically treated with proteases (for example, a collagenase or trypsin or pepsin), glycosaminoglycanases or a combination of proteases and glycosaminoglycanases. Optionally, other appropriate enzymes can be used alone or in combination with proteases and glycosaminoglycanases. The tissue digest can be optionally filtered to provide a homogenous solution of partially solubilized submucosa.

The viscosity of fluidized submucosa can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by dialyzing the digested material and then adjusting the pH of such solutions to about 5.0 to about 9.0.

Urinary bladder or stomach submucosa can also be in the form of an extract. For example, the preparation of extracts of submucosa tissue is described in PCT Application No. PCT/US97/22721, published as WO 98/25964 on Jun. 18, 1998 which is incorporated herein by reference. Briefly, urinary bladder or stomach submucosa can be suspended in an extraction buffer (see Example 1) with agitation for about 24 hours at 4° C. The extraction mixture can be centrifuged at 12,000×g for about 30 minutes at 4° C. and the supernatant collected. The insoluble material can then be washed with the extraction buffer and the centrifugation step repeated and the wash combined with the original supernatant. The supernatant can be dialyzed (MWCO about 3500) extensively against deionized water and the dialyzate centrifuged at 12,000×g. The supernatant can be used immediately or lyophilized for storage. The fluidized and gel forms of urinary bladder or stomach submucosa, and the extracts of these submucosal tissues may retain biologically active agents such as growth factors including transforming growth factor (TGF) β, TGF β-related proteins, and fibroblast growth factor. Urinary bladder or stomach submucosa tissue in fluidized form or in the form of a gel, an extract, or a powder can be used to culture endothelial cells and the preselected cell population in vitro prior to implantation of the graft construct in accordance with the invention.

The present invention also contemplates the use of powder forms of submucosa. In one embodiment a powder form of submucosa is prepared by pulverizing submucosa under liquid nitrogen to produce particles ranging in size from 0.1 to 1 $mm^2$. The particulate composition is then lyophilized overnight and sterilized to form a solid substantially anhydrous particulate composite. Alternatively, a powder form of submucosa can be formed from fluidized submucosa by drying the suspensions or solutions of comminuted submucosa.

EXAMPLE 1

Preparation of Urinary Bladder and Stomach Submucosa Compositions

Preparation of Urinary Bladder Submucosa

Urinary bladder submucosa was prepared from porcine urinary bladder from a local meat processing plant. The excised urinary bladder was rinsed free of contents, everted and the superficial layers of the mucosa were removed by mechanical delamination. The tissue was reverted to its original orientation and the external muscle layer removed. The prepared urinary bladder was split open and rinsed extensively in water to lyse any cells associated with the submucosa matrix and to eliminate cell degradation products.

Alternatively, urinary bladder tissue retaining both the submucosal layer and the epithelial basement membrane can be prepared according to the method of Spievack described in WO 01/45765 and incorporated herein by reference. According to this method urinary bladder submucosa tissue retaining the epithelial basement membrane can be prepared by soaking the tissue in a de-epithelializing solution, for example, 1 N saline. In another embodiment, urinary bladder tissue can be soaked in 1 N saline and subjected to enzymatic and mechanical delamination steps to remove additional layers, or portions thereof, subadjacent to the submucosal layer. Either of these procedures results in a preparation that includes the urinary bladder or stomach submucosa layer and the epithelial basement membrane.

Such preparations are used in the graft constructs in accordance with the invention as described below. For preparing fluidized or gel forms of urinary bladder submucosa or for extracts of urinary bladder submucosa, immediately after rinsing, the urinary bladder submucosa is typically first frozen in liquid nitrogen and stored at −80° C. The frozen tissue is sliced into 1 cm cubes, pulverized under liquid nitrogen with an industrial blender to particles less than 2 mm$^2$ and stored at −80° C. prior to use. The preparation of fluidized or gel forms of urinary bladder submucosa and of extracts of urinary bladder submucosa is described below.

Preparation of Stomach Submucosal Tissue

The stomach was first removed from the pigs by transecting the esophagus and small intestine at their respective entrance and exit points on the stomach. Any excess mesentery tissue or fat was removed from the abluminal surface of the stomach and the contents of the stomach were emptied and any remaining residues were removed from the inside of the stomach by rinsing with running tap water. The stomach was then everted to expose the inside (luminal) surface of the stomach and was cut just to the sphincter at the end of the esophagus and just distal to the sphincter that forms the exit point of the stomach. The stomach is typically left whole, however the stomach can also be cut and flattened prior to removal of unwanted tissues. The luminal surface of the stomach was subjected to abrasion using a blunt instrument or hemostats to remove the inner layers of the stomach including at least the luminal portion of the tunica mucosa. The stomach tissue was everted again to return the luminal surface of the stomach to the interior of the graft construct. A small cut was then made in the exterior muscle fiber layer. The muscle layers were then delaminated from the submucosal tissue mechanically or enzymatically. The remaining tissue is pinkish-white in color. Alternatively, stomach submucosa tissue retaining the epithelial basement membrane can be prepared according to the methods described in Spievack et al. as discussed above.

During the preparation of the stomach tissue care was taken to maintain hydration of the tissue by periodically bathing the tissue with water. The stomach submucosa tissue was rinsed in running tap water for approximately two hours to remove any blood or loose tissue tags. After rinsing the tissue should appear white, but if the tissue remains pinkish in color the tissue is rubbed under water until the tissue appears white. After rinsing was complete, excess water was removed by ringing the tissue by hand or by the use of mechanical ringers. Such preparations are used in the graft constructs in accordance with the invention. For preparing fluidized or gel forms of stomach submucosa or for extracts of stomach submucosa, the tissue is typically first frozen in liquid nitrogen and stored in liquid nitrogen at −80° C. The frozen tissue is sliced into 1 cm cubes, pulverized under liquid nitrogen with an industrial blender to particles less than 2 mm$^2$ and stored at −80° C. prior to use. The preparation of fluidized or gel forms of stomach submucosa and of extracts of stomach submucosa is described below.

Preparation of Fluidized Urinary Bladder or Stomach Submucosa

Partial digestion of the pulverized material was performed by adding 5 g of powdered tissue to a 100 ml solution containing 0.1% pepsin in 0.5 M acetic acid and digesting for 72 hours at 4° C. Following partial digestion, the suspension was centrifuged at 12,000 rpm for 20 minutes at 4° C. and the insoluble pellet discarded. The supernatant was dialyzed against several changes of 0.01 M acetic acid at 4° C. (MWCO 3500). The solution was sterilized by adding chloroform (5 ml chloroform to 900 ml of 0.01 M acetic acid) to the dialysis hydrolysate. Dialysis of the hydrolysate was continued with two additional changes of sterile 0.01 M acetic acid to eliminate the chloroform. The contents of the dialysis bag were then transferred aseptically to a sterile container. The resultant fluidized composition was stored at 4° C.

Preparation of Urinary Bladder and Stomach Submucosa Gel Compositions

To prepare the gel form of the urinary bladder or stomach submucosa, 8 mls of fluidized submucosa was mixed with 1.2 ml 10×PBS buffer (10× phosphate buffered saline containing 5 mg/L phenol red); 0.04 N HCl (approx 1.6 ml) was added to adjust the pH to between 6.6 and 7.4 and then 0.05 N NaOH (approx. 1.2 ml) was added to shift the pH to >8. The final volume was adjusted to 12 ml with water.

Preparation of Extracts of Urinary Bladder or Stomach Submucosa

Extraction buffers used for these studies included 4 M guanidine, 2 M urea, 2 M MgCl$_2$ and 2 M NaCl each prepared in 50 mM Tris-HCl, pH 7.4. Urinary bladder or stomach submucosa powder was suspended in extraction buffers (25% w/v) containing phenylmethyl sulphonyl fluoride, N-ethylnaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuiged at 12,000×g to remove any insoluble material and the supernatant was used immediately or lyophilized for storage.

EXAMPLE 2

Growth of Endothelial Cells

Urinary bladder or stomach submucosa is harvested and prepared from freshly euthanatized pigs as described above. Following sterilization via various techniques (gamma irradiation, peracetic acid, etc.), the tissue is clamped within a polypropylene frame to create a flat surface area (50 mm2) for cell growth. The frame is submerged in tissue culture medium to allow access of medium nutrients to both surfaces of the urinary bladder or stomach submucosa tissue. Endothelial cells and smooth muscle cells are seeded (at 3×104 cells/tissue section) on the submucosa tissue and then placed in a 5% CO2, 95% air incubator at 37° C. Following various periods of time, the seeded urinary bladder or stomach submucosa tissue is fixed in 10% neutral buffered formalin, embedded in paraffin, and sectioned (6 um). Various histological and immunohistochemical staining procedures are done to determine the cell growth characteristics. Vessels or vessel-like structures are observed using these procedures.

EXAMPLE 3

Growth of Endothelial Cells

Figure 2:
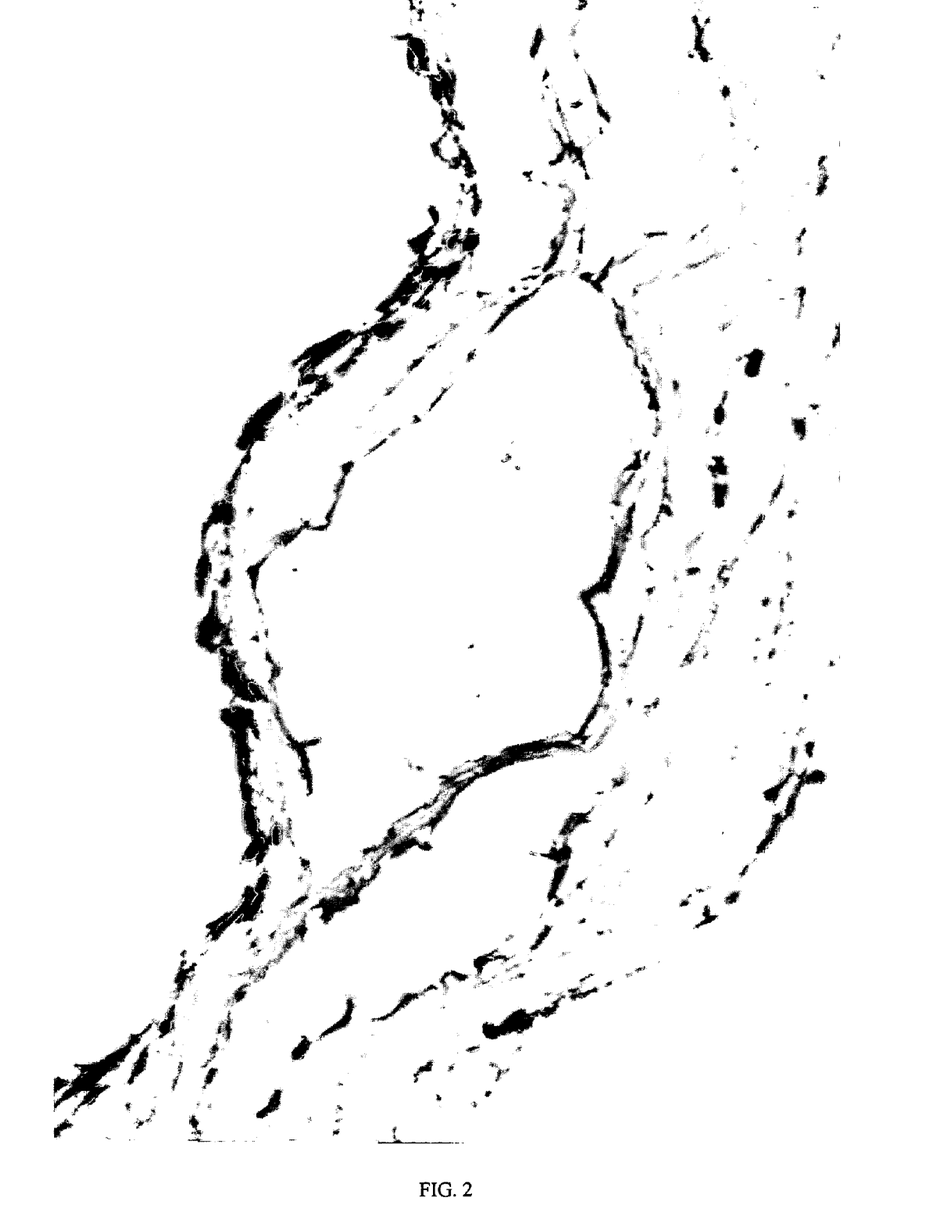
FIG. 2 is a photomicrograph showing a histological section of a tissue graft seeded with endothelial cells.
Figure 3:
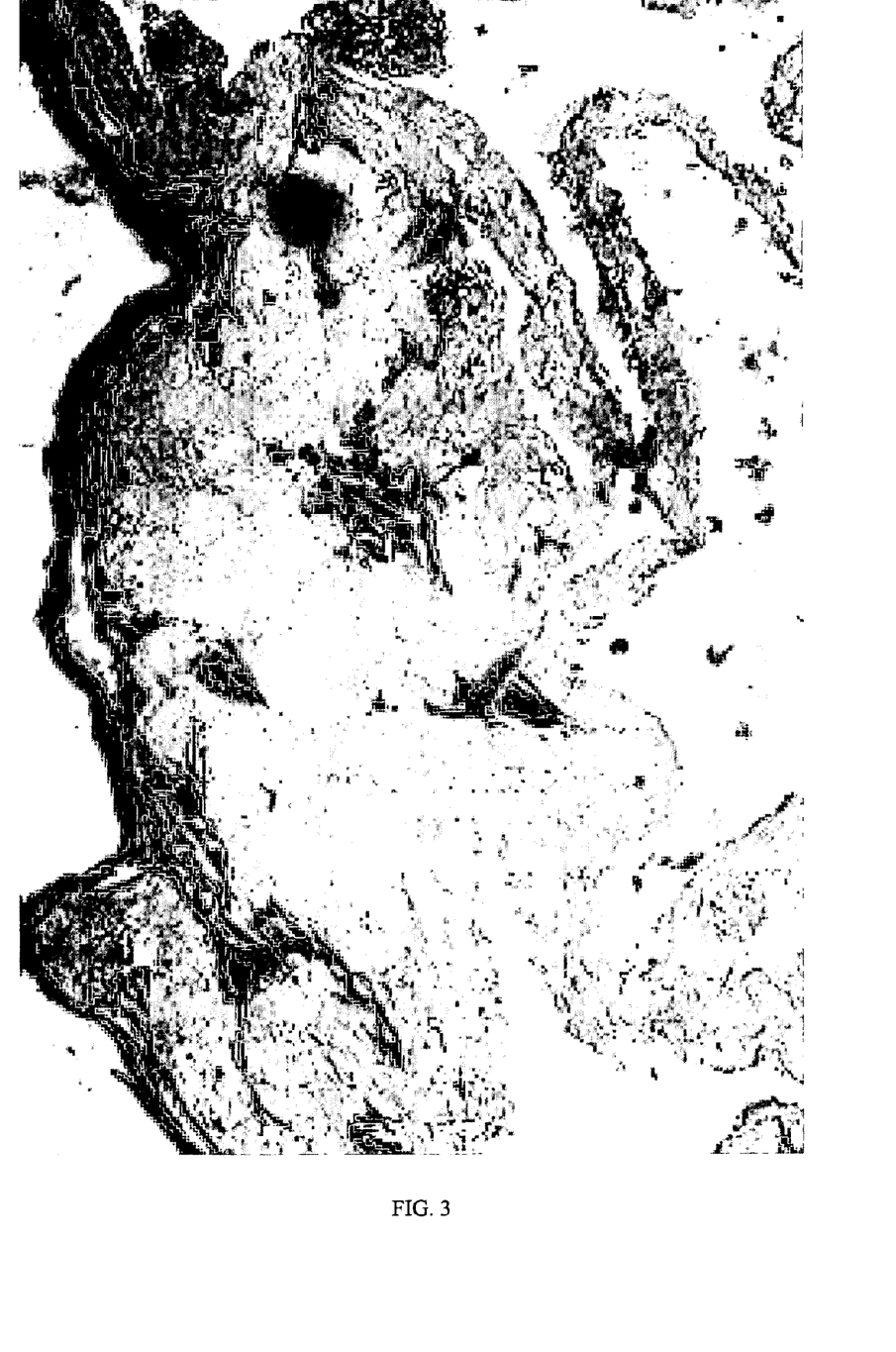
FIG. 3 is a photomicrograph showing a histological section of a tissue graft seeded with endothelial cells and 3T3 cells.

Urinary bladder submucosa was harvested and prepared from freshly euthanatized pigs as described above. Following sterilization via various techniques (gamma irradiation, peracetic acid, etc.), the tissue was clamped within a polypropylene frame to create a flat surface area (50 mm$^2$) for cell growth. The frame was submerged in tissue culture medium to allow access of medium nutrients to both surfaces of the urinary bladder submucosa tissue. Human microvascular endothelial cells were seeded on one surface of the urinary bladder submucosa tissue and 3T3 cells were seeded on the other surface (both cell types were seeded at 1×10$^6$ cells/tissue section) and then the tissue section was placed in a 5% $CO_2$, 95% air incubator at 37° C. After 7 days of growth, the seeded urinary bladder submucosa tissue was fixed in 10% neutral buffered formalin, embedded in paraffin, and sectioned (6 um). Various histological and immunohistochemical staining procedures were done to determine the cell growth characteristics. As shown in FIG. 2, the endothelial cells, seeded alone on the urinary bladder submucosa in the absence of any additional cell type, grew on the urinary bladder submucosa surface without invading the matrix. As shown in FIG. 3, when 3T3 cells were seeded on the opposite surface, the cells invaded the matrix and formed vessels or vessel-like structures. These results indicate that the capacity of endothelial cells to form vessels or vessel-like structures in the graft material is enhanced when the endothelial cells are grown on the graft material in the presence of another cell type.

What is claimed is:

1. A tissue graft construct for use in repairing diseased or damaged tissues, said tissue graft construct comprising a matrix composition comprising a material selected from the group consisting of urinary bladder submucosa tissue and stomach submucosa tissue, wherein the tissue graft construct further comprises added endothelial cells, and at least one additional preselected, exogenous population of cells wherein the matrix composition is seeded with the additional preselected population of cells after the matrix composition is seeded with the endothelial cells, wherein said exogenous population of cells enhances the initiation of vessels or vessel-like structures in said graft construct.

2. The graft construct of claim 1 wherein the at least one additional preselected, exogenous population of cells comprises a population of cells selected from the group consisting of keratinized epithelial cells, non-keratinized epithelial cells, and mesodermally-derived cells.

3. The graft construct of claim 1 wherein the at least one additional preselected, exogenous population of cells comprises a population of smooth muscle cells.

4. The graft construct of claim 1 wherein the at least one additional preselected, exogenous population of cells comprises a population of smooth muscle cell progenitor cells.

5. The graft construct of claim 1 wherein the urinary bladder or stomach submucosa tissue is delaminated from the tunica muscularis layer and at least the luminal portion of the tunica mucosa layer of said submucosa tissues.

6. The graft construct of claim 1 wherein the exogenous population of cells is a population of fibroblasts.

7. A tissue graft construct for use in repairing diseased or damaged tissues, said tissue graft construct comprising a matrix composition comprising a material selected from the group consisting of urinary bladder submucosa tissue and stomach submucosa tissue, wherein the tissue graft construct further comprises added endothelial cells, and at least one additional preselected, exogenous population of cells and wherein the matrix composition is seeded with the endothelial cells after the matrix composition is seeded with the additional preselected population of cells.

8. The graft construct of claim 7 wherein the at least one additional cell population comprises a population of cells selected from the group consisting of keratinized epithelial cells, non-keratinized epithelial cells, mesodermally-derived cells, smooth muscle cells, and smooth muscle cell progenitor cells.

9. The graft construct of claim 7 wherein the exogenous population of cells is a population of fibroblasts and the material is selected from the group consisting of urinary bladder submucosa tissue and stomach submucosa tissue.

10. The graft construct of claim 9 wherein the urinary bladder or stomach submucosa tissue is delaminated from the tunica muscularis layer and at least the luminal portion of the tunica mucosa layer of said submucosa tissues.

11. A tissue graft construct for use in repairing diseased or damaged tissues, said tissue graft construct comprising a matrix composition comprising a material selected from the group consisting of urinary bladder submucosa tissue and stomach submucosa tissue, wherein the tissue graft construct further comprises added endothelial cells, and at least one additional preselected, exogenous population of cells and wherein the matrix composition is seeded with the endothelial cells and the additional preselected population of cells simultaneously or nearly simultaneously.

12. The graft construct of claim 11 wherein the at least one additional cell population comprises a population of cells selected from the group consisting of keratinized epithelial cells, non-keratinized epithelial cells, mesodermally-derived cells, smooth muscle cells, and smooth muscle cell progenitor cells.

13. The graft construct of claim 11 wherein the exogenous population of cells is a population of fibroblasts and the material is selected from the group consisting of urinary bladder submucosa tissue and stomach submucosa tissue.

14. The graft construct of claim 13 wherein the urinary bladder or stomach submucosa tissue is delaminated from the tunica muscularis layer and at least the luminal portion of the tunica mucosa layer of said submucosa tissues.

15. A tissue graft construct having vessel-like structures for use in repairing diseased or damaged tissues, said tissue graft construct comprising a matrix composition comprising a material selected from the group consisting of urinary bladder submucosa tissue and stomach submucosa tissue, wherein the tissue graft construct further comprises added endothelial cells, and at least one additional preselected, exogenous population of cells wherein said at least one additional preselected, exogenous population of cells enhances the initiation of formation of said vessel-like structures in said graft construct.

16. The graft construct of claim 15 further comprising a heparinase.

17. The graft construct of claim 15 further comprising a growth factor selected from the group consisting of vascular endothelial cell-derived growth factor, platelet-derived growth factor, a platelet-derived growth factor-like molecule, transforming growth factor β, and a serum growth factor.

18. The graft construct of claim 15 wherein the at least one additional cell population comprises a population of cells selected from the group consisting of keratinized epithelial cells, non-keratinized epithelial cells, mesodermally-derived cells, smooth muscle cells, and smooth muscle cell progenitor cells.

19. The graft construct of claim 15 wherein the exogenous population of cells is a population of fibroblasts and the material is selected from the group consisting of urinary bladder submucosa tissue and stomach submucosa tissue.

20. The graft construct of claim 19 wherein the urinary bladder or stomach submucosa tissue is delaminated from the tunica muscularis layer and at least the luminal portion of the tunica mucosa layer of said submucosa tissues.

21. A method of preparing a tissue graft construct having vessel-like structures for use in repairing diseased or damaged tissues, said method comprising the step of seeding in vitro a matrix composition comprising a material selected from the group consisting of urinary bladder submucosa tissue and stomach submucosa tissue, with a population of endothelial cells, and at least one additional preselected, exogenous population of cells wherein said at least one additional preselected, exogenous population of cells enhances the initiation of formation of said vessel-like structures in said graft construct.

22. The method of claim 21 wherein the at least one additional cell population comprises a population of cells selected from the group consisting of keratinized epithelial cells, non-keratinized epithelial cells, mesodermally-derived cells, smooth muscle cells, and smooth muscle cell progenitor cells.

23. The method of claim 21 wherein the exogenous population of cells is a population of fibroblasts and the material is selected from the group consisting of urinary bladder submucosa tissue and stomach submucosa tissue.

24. The method of claim 23 wherein the urinary bladder or stomach submucosa tissue is delaminated from the tunica muscularis layer and at least the luminal portion of the tunica mucosa layer of said submucosa tissues.

25. The method of claim 21 wherein the graft construct further comprises a heparinase.

26. The method of claim 21 wherein the graft construct further comprises a growth factor selected from the group consisting of vascular endothelial cell-derived growth factor, platelet-derived growth factor, a platelet-derived growth factor-like molecule, transforming growth factor β, and a serum growth factor.

* * * * *